United States Patent [19]
Kirby et al.

[11] Patent Number: 6,133,294
[45] Date of Patent: Oct. 17, 2000

[54] 2-METHOXYIMINO-2-(PYRIDINYLOXYMETHYL) PHENYL ACETAMIDES WITH 5 MEMBERED HETEROCYCLIC RINGS ON THE PYRIDINE RING

[76] Inventors: Neil V. Kirby, 13911 Stonemill Cir., Carmel, Ind. 46032; Irene M. Morrison, 8224 Glenwillow La. #206, Indianapolis, Ind. 46278; Emily J. Canada, 5523 N. Arlington Ave., Indianapolis, Ind. 46226; Mary E. Pieczko, 5323 Holly Springs Dr. West, Indianapolis, Ind. 46254; Gary D. Gustafson, 4572 Ivywood Ct., Zionsville, Iowa 46077; David H. Cooper, 2243 Fullerton Cir., Indianapolis, Ind. 46214; Jenifer L. Adamski, 4813 N. Broadway, Indianapolis, Ind. 46205; John T. Mathieson, 6527 Donnelly Dr., Brownsburg, Ind. 46112; Christopher S. Galka, 3024 Woodspring Dr., Carmel, Ind. 46033

[21] Appl. No.: 09/397,564

[22] Filed: Sep. 16, 1999

Related U.S. Application Data

[60] Provisional application No. 60/100,666, Sep. 16, 1998.

[51] Int. Cl.⁷ .................. A61K 31/44; C07D 413/14
[52] U.S. Cl. .................. 514/340; 546/269.4
[58] Field of Search .............. 546/270.1, 268.7, 546/269.4; 504/244; 514/340

[56] References Cited

U.S. PATENT DOCUMENTS

| | | | |
|---|---|---|---|
| 5,021,581 | 6/1991 | Clough et al. | 549/309 |
| 5,089,510 | 2/1992 | Tapolczay et al. | 514/345 |
| 5,157,037 | 10/1992 | Schuetz et al. | 514/269 |
| 5,185,342 | 2/1993 | Hayase et al. | 514/274 |
| 5,334,577 | 8/1994 | Wenderoth et al. | 504/130 |
| 5,442,063 | 8/1995 | Takase et al. | 544/333 |
| 5,466,693 | 11/1995 | Warrington et al. | 514/269 |
| 5,470,819 | 11/1995 | Anthony at al. | 504/244 |
| 5,585,513 | 12/1996 | Matthews et al. | 560/60 |
| 5,770,614 | 6/1998 | Murabayashi et al. | 514/348 |
| 5,856,573 | 1/1999 | Takase et al. | 514/169 |

FOREIGN PATENT DOCUMENTS

| | | |
|---|---|---|
| 0 781 764 A1 | 7/1997 | European Pat. Off. . |
| WO 97/01538 | 1/1997 | WIPO . |
| WO 97/29088 | 8/1997 | WIPO . |
| WO 98/23350 | 6/1998 | WIPO . |
| WO 98/33772 | 8/1998 | WIPO . |
| WO 99/25713 | 5/1999 | WIPO . |

OTHER PUBLICATIONS

"Strobilurins: Evolution of a New Class of Active Substances ", Angew Chem. Int. Ed. 1999, 38. 1328–1349.
"The Strobilurin Fungicides", Fugicidal Activity, 1998.
"Structure and Fungicidal Activities of 2–Methoxyimino–N–methyl–2–[2–(substituted pyridyloxymethyl)phenyl]acetamide Derivatives", J. Petsticide Sci. 23. 379–385 (1998).
Extended Summaries: IUPAC Congress, Pestic Sci 55: 343–389 (1999).

*Primary Examiner*—Zinna Northington Davis
*Assistant Examiner*—Binta Robinson
*Attorney, Agent, or Firm*—Carl D. Corvin

[57] ABSTRACT

The present invention provides novel 2-methoxyimino-2-(pyridinyloxymethyl)phenyl acetamide compounds with 5 membered heterocyclic rings on the pyridine ring, their use as fungicidal compounds, and their use in fungicidal compositions comprising at least one of the 2-methoxyimino-2-(pyridinyloxymethyl)phenyl acetamide compounds as the active ingredient.

14 Claims, No Drawings

2-METHOXYIMINO-2-(PYRIDINYLOXYMETHYL) PHENYL ACETAMIDES WITH 5 MEMBERED HETEROCYCLIC RINGS ON THE PYRIDINE RING

PRIORITY CLAIM

This application claims a priority based on provisional application 60/100,666 abandoned which was filed in the U.S. Patent and Trademark Office on Sep. 16, 1998.

BACKGROUND OF THE INVENTION

The present invention provides novel 2-methoxyimino-2-(pyridinyloxymethyl)phenyl acetamide compounds with 5 membered heterocyclic rings on the pyridine ring, their use as fungicidal compounds, and their use in fungicidal compositions comprising at least one of the 2-methoxyimino-2-(pyridinyloxymethyl)phenyl acetamide compounds as the active ingredient.

SUMMARY OF THE INVENTION

This invention provides novel 2-methoxyimino-2-(pyridinyloxymethyl)phenyl acetamide compounds of formula (1), below

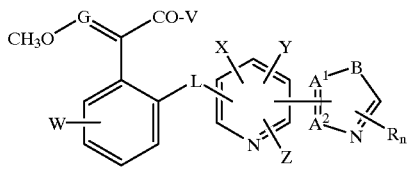

Formula (1)

wherein
L is —O—, —CH$_2$—, —SO$_n$—, —CH$_2$O—, —OCH$_2$—, —CH$_2$S—, —SCH$_2$—, —CH=CH—, —C≡C—, or

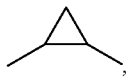

wherein
n is an integer 0–2;
X, Y, and Z are each independently H, C$_{1-6}$ alkyl, C$_{1-6}$ alkoxy, halo-C$_{1-6}$ alkyl, halo-C$_{1-6}$ alkoxy, halo, nitro, carbo-C$_{1-6}$ alkoxy, cyano, C$_{1-6}$ alkylthio, or halo-C$_{1-6}$ alkylthio;
W is H, halogen, C$_{1-4}$ alkyl, C$_{1-4}$ alkoxy, halo-C$_{1-4}$ alkyl, or C$_{1-4}$ alkylthio;
R is H, C$_{1-10}$ alkyl, alkenyl cycloalkyl, haloalkyl, alkoxyalkyl, optionally substituted phenoxyalkyl, alkylthioalkyl, optionally substituted phenylthioalkyl, cyanoalkyl, optionally substituted benzyl, alkoxycarbonyl, optionally substituted phenyl, optionally substituted heterocycle;
n is 0–2;
A$^1$, A$^2$ are independently N, CR$^1$;
B is O, S, NR$^1$;
G is CH or N;
V is OCH$_3$ or NHCH$_3$;
R$^1$ is C$_{1-6}$ alkyl, C$_{1-6}$ alkenyl, C$_{1-6}$ alkynyl, optionally substituted phenyl, optionally substituted benzyl.

The present invention also provides compositions comprising one or more compounds of Formula (1) in combination with phytologically-acceptable carriers and/or diluents. Methods for the use of compounds of formula (1) and compositions comprising one or more compounds of formula (1) are also provided.

DETAILED DESCRIPTION OF THE INVENTION

Throughout this document, all temperatures are given in degrees Celsius and all percentages are weight percentages, unless otherwise stated.

The term "halogen" or "halo" refers to F, Cl, I, or Br.

The term "alkyl", "alkenyl", or "alkynyl" refers to a straight chain or branched chain carbon radical containing the designated number of carbon atoms.

The term "alkoxy" refers to a straight or branched chain alkoxy group.

The term "halo alkyl" refers to a straight or branched alkyl group substituted with one or more halo atoms. The term "halo alkoxy" refers to an alkoxy group substituted with one or more halo atoms.

The term "aryl" or "Ph" refers to a phenyl group. The term "substituted aryl" refers to a phenyl group substituted with C$_1$–C$_6$ alkyl, C$_1$–C$_6$ alkoxy, halo-C$_1$–C$_6$ alkyl, halo-C$_1$–C$_6$ alkoxy, halo, nitro, carbo-C$_1$–C$_6$ alkoxy, or cyano. The term "heteroaryl" refers to pyridyl, pyridinyl, pyrazinyl or pyridazinyl.

The term "Me" refers to a methyl group. The term "Et" refers to an ethyl group. The term "Pr" refers to a propyl group. The term "Bu" refers to a butyl group.

The term "EtOAc" refers to ethyl acetate.

The term "ppm" refers to parts per million. The term, "psi" refers to pounds per square inch.

The term "M.P." refers to melting point. The term "bp" refers to boiling point.

While all the compounds of this invention have fungicidal activity, certain classes of compounds may be preferred for reasons such as, for example, greater efficacy or ease of synthesis.

A preferred class includes those compounds of Formula (2), below

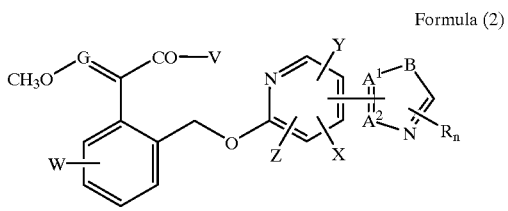

Formula (2)

wherein the substituents are as defined in Formula (1), above.

A more preferred class includes those compounds Formula (3), below

Formula (3)

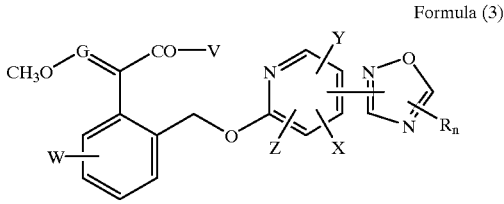

wherein the substituents are as defined in Formula (1), above.

A next more preferred class includes those compounds of Formula (4), below

Formula (4)

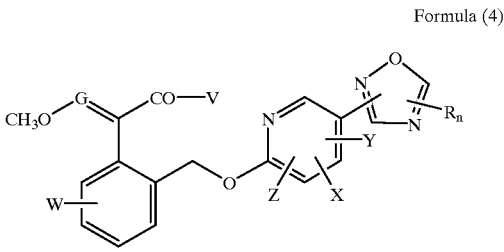

wherein the substituents are as defined in Formula (1), above.

A next more preferred class includes those compounds of Formula (5), below

Formula (5)

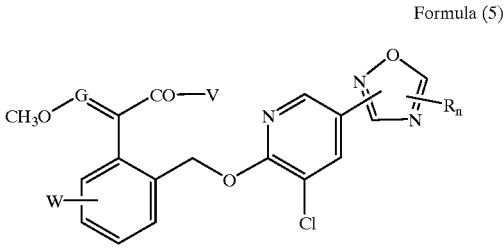

wherein the substituents are as defined in Formula (1), above.

A next more preferred class includes those compounds of Formula (6), below

Formula (6)

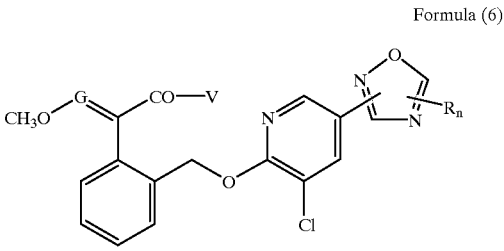

wherein the substituents are as defined in Formula (1), above.

EXAMPLES

Compounds of the present invention may be prepared by routes commonly known in the art using commercially available or readily synthesized starting materials. Such general procedures are described in Scheme 1 and Scheme 2, below, wherein the substituents are as described in formula (1), above, and V is a leaving group, such as, for example, F, Cl, or $SO_2CH_3$.

Scheme 1

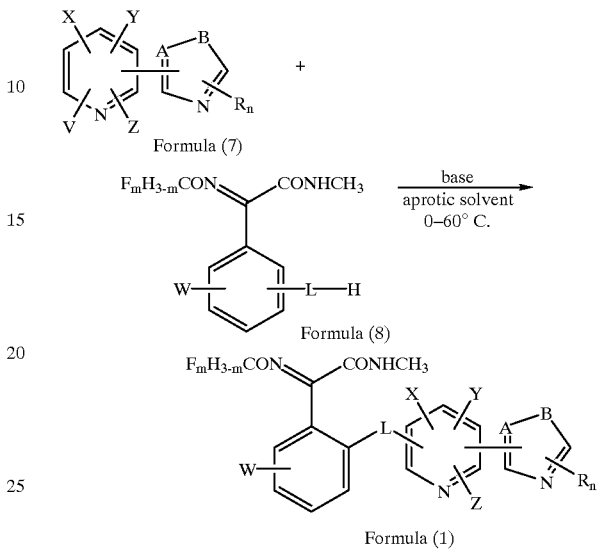

A compound of formula (8) is reacted with an appropriately substituted pyridine derivative of formula (7) in the presence of a base in an aprotic solvent. Examples of an appropriate solvent for this reaction would include, but are not restricted to tetrahydrofuran, dimethyl sulphoxide, acetone, acetonitrile, dimethyl formamide, N-methylpyrollidinone. Examples of an appropriate base for this reaction would include, but are not restricted to sodium hydride, potassium hydride, potassium carbonate, an alkoxide salt, or a tertiary amine derivative such as triethylamine.

The following examples further illustrate this invention. The examples should not be construed as limiting the invention in any manner.

Example 1

5,6-Dichloro-N-hydroxy-3-pyridinecarboximidamide

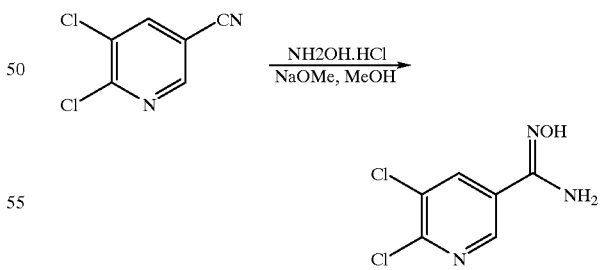

Hydroxylamine hydrochloride (2.6 g, 0.038 mol) was slurried in methanol (75 mL) and sodium methoxide (2.0 g, 0.037 mol) added. The mixture was stirred for half an hour and 5,6-dichloro-3-pyridinecarbonitrile (4.3 g, 0.025 mol) added. The mixture was stirred at room temperature overnight and filtered. The precipitate was washed with water and methanol and dried to give the desired product (4.2 g, 82%) as a white solid, MP 182–184° C.

Example 2

5-(t-Butyl)-3-(5,6-dichloro-3-pyridinyl)-1,2,4-oxadiazole

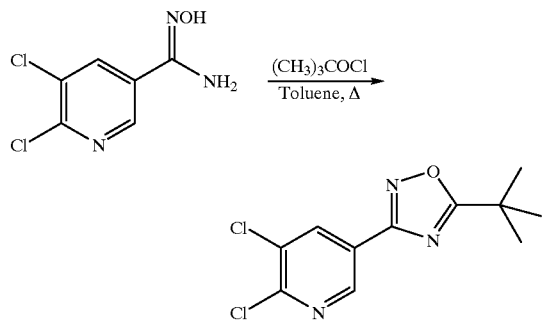

5,6-Dichloro-N-hydroxy-3-pyridinecarboximidamide (3.0 g, 0.015 mol) was slurried in toluene (30 mL) and trimethylacetyl chloride (1.93 g, 0.016 mol) added. The mixture was stirred at room temperature for one hour and then heated under reflux conditions for four hours. This was then cooled and filtered through Celite, washing with additional toluene (20 mL). Evaporation of the solvent under reduced pressure and purification of the residue by chromatography over silica (0–10% ethyl acetate:hexane) gave the desired product as a white solid (2.77 g, 68%).

Example 3

5-Chloro-2-methylthio-3-pyridinecarbonitrile

5,6-Dichloro-3-pyridinecarbonitrile (1.73 g, 0.01 mol) was dissolved with stirring in dimethyl sulphoxide (25 mL) and sodium methanethiolate (0.77 g, 0.011 mol) added. The reaction mixture was stirred at room temperature for two hours and poured onto ice (100 g). The mixture was extracted with dichloromethane (50 mL), and the organic extract washed with water (100 mL), and brine, and dried over anhydrous sodium sulphate. Evaporation of the solvent under reduced pressure and recrystallisation of the residue from ethyl acetate:hexane gave the desired product (1.3 g, 71%) as a cream solid, MP 147–9° C.

Example 4

5-Chloro-6-methylthio-N-hydroxy-3-pyridinecarboximidamide

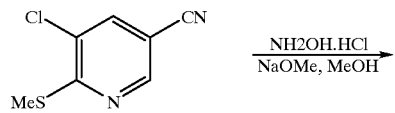

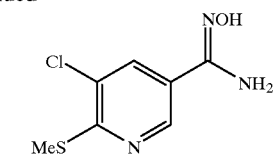

A mixture of 5-chloro-2-methylthio-3-pyridinecarbonitrile (1.04 g, 5.6 mmol), potassium carbonate (3.88 g, 29 mmol), hydroxylamine hydrochloride (1.95 g, 28 mmol) and ethanol (20 mL) was heated under reflux for eight hours, and stirred at room temperature overnight. It was then poured into water (100 mL), filtered, and the precipitate recrystallised from methanol to give the desired product (1.0 g, 82%) as a white solid, MP 139–143° C.

Example 5

5-(t-Butyl)-3-(5-chloro-6-methylthio-3-pyridinyl)-1,2,4-oxadiazole

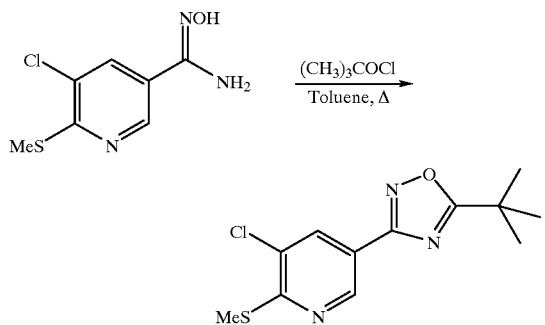

5-Chloro-6-methylthio-N-hydroxy-3-pyridinecarboximidamide (1.0 g, 4.6 mmol) was slurried in toluene (20 mL) and trimethylacetyl chloride (0.61 g, 5.1 mmol) added. The mixture was stirred at room temperature for one hour and then heated under reflux conditions for four hours. This was then cooled and filtered through Celite, washing with additional toluene (20 mL). Evaporation of the solvent under reduced pressure and purification of the residue by chromatography over silica (0–10% ethyl acetate:hexane) gave the desired product as a white solid (0.77 g, 59%).

Example 6

5-(t-Butyl)-3-(5-chloro-6-methylsulphonyl-3-pyridinyl)-1,2,4-oxadiazole

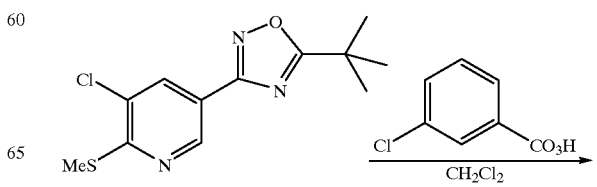

-continued

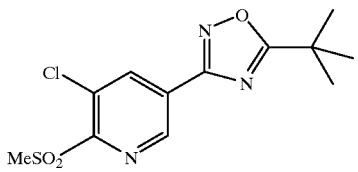

5-(t-Butyl)-3-(5-chloro-6-methylthio-3-pyridinyl)-1,2,4-oxadiazole (0.80 g, 2.82 mmol) was dissolved with stirring in dichloromethane (50 mL) and 55% m-chloroperoxybenzoic acid (4.2 g, 0.013 mol) added. The mixture was stirred at room temperature overnight, and 10% sodium carbonate solution (50 mL) added. This was then stirred at room temperature and separated. The organic phase was washed three times with 2M sodium hydroxide solution (50 mL) and once with saturated brine (50 mL). It was then dried over anhydrous sodium sulphate and the solvent evaporated under reduced pressure to give the desired product (0.8 g, 90%) as a viscous oil.

Example 7

Benzeneacetamide, 2-[[[3-chloro-5-(5-t-butyl-1,2,4-oxadiazol-3-yl)-2-pyridinyl]oxy]methyl]-α-(methoxyimino)-N-methyl-

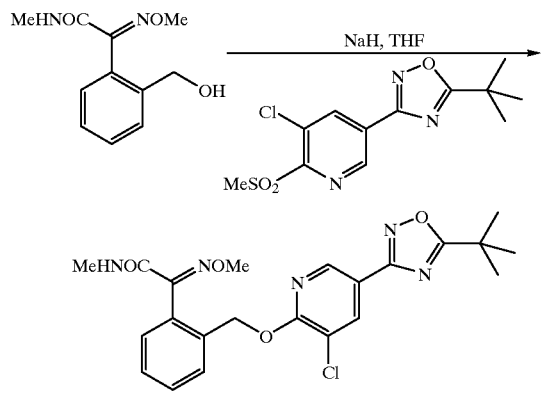

2-(Hydroxymethyl)-α-(methoxyimino)-N-methylbenzeneacetamide (0.71 g, 3.2 mmol) was dissolved with stirring in dry THF (20 mL) and 60% sodium hydride (0.15 g, 3.8 mmol) added. The mixture was stirred for thirty minutes and a solution of 5-(t-Butyl)-3-(5-chloro-6-methylsulphonyl-3-pyridinyl)-1,2,4-oxadiazole (1.0 g, 3.2 mmol) in dry THF (10 mL) added. The mixture was stirred at room temperature for three hours and poured into water. The mixture was extracted twice with ethyl acetate (50 mL) and the organic extracts were washed twice with water (50 mL) and saturated brine (50 mL). The solution was dried over anhydrous sodium sulphate, and evaporated to dryness. Purification of the residue by chromatography over silica, eluting with 10–35% ethyl acetate:pentane, gave the desired product as a white solid (0.73 g, 50%), MP 138–140° C.

Example 8

3-t-Butyl-5-(5,6-dichloro-3-pyridyl)-1,2,4-oxadiazole

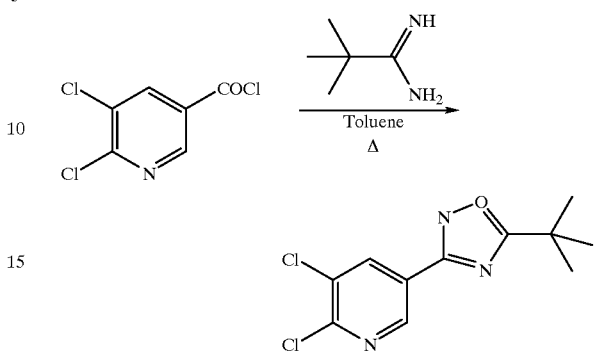

A mixture of 5,6-dichloro-pyridine-3-carbonyl chloride (1.8 g, 8.6 mmol) and N-hydroxy-2,2-dimethylpropanimidamide (1.0 g, 8.6 mmol) in toluene (40 mL) was stirred at room temperature for two hours and then heated under reflux for four hours. The mixture was cooled to room temperature and filtered through celite, the solids being washed with toluene (20 mL). Evaporation of the combined filtrates under reduced pressure gave the desired product (1.3 g, 56%) as a clear oil which crystallised on standing to a white solid, MP 98–101° C.

Example 9

Benzeneacetamide, 2-[[[3-chloro-5-(3-t-butyl-1,2,4-oxadiazol-5-yl)-2-pyridinyl]oxy]methyl]-α-(methoxyimino)-N-methyl-

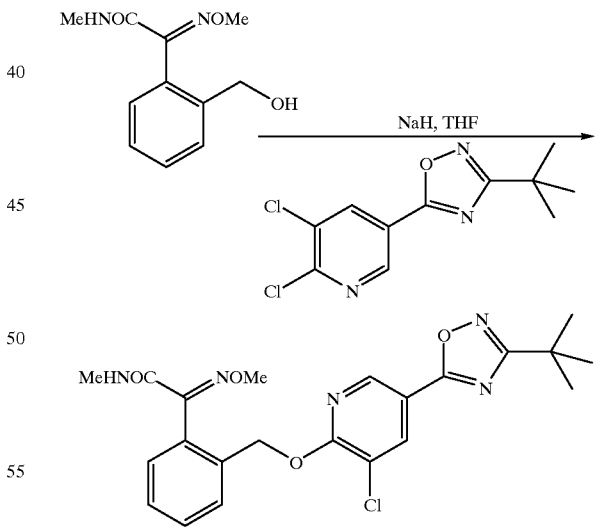

2-(Hydroxymethyl)-α-(methoxyimino)-N-methylbenzeneacetamide (1.0 g, 4.5 mmol) was dissolved with stirring in dry THF (35 mL) and 60% sodium hydride (0.22 g, 5.5 mmol) added. The mixture was stirred for thirty minutes and a solution of 3-t-butyl-5-(5,6-dichloro-3-pyridyl)-1,2,4-oxadiazole (1.22 g, 4.5 mmol) in dry THF (10 mL) added. The mixture was stirred at room temperature overnight and poured into water. The mixture was extracted twice with ethyl acetate (50 mL) and the organic extracts were washed twice with water (50 mL) and saturated brine (50 mL). The solution was dried over anhydrous sodium sulphate, and evaporated to dryness. Purification of the residue by chromatography over silica, eluting with 10–40% ethyl acetate:pentane, gave the desired product as a white solid (1.4 g, 68%), MP 138–140° C.

Example 10

N-[1-(Dimethylamino)ethylidene]-5,6-dichloro-3-pyridinecarboxamide

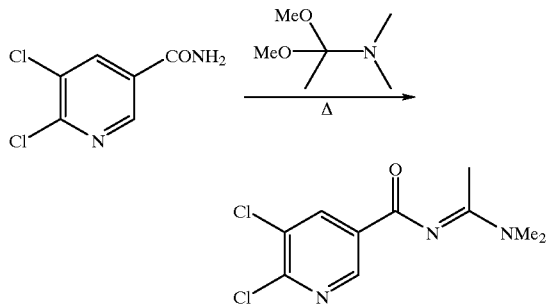

A mixture of 5,6-dichloro-3-pyridinecarboxamide (4.0 g, 0.02 mol), dimethylacetamide dimethyl acetal (8 mL) was heated in an oil bath at 120° C. for three hours. The reaction mixture was cooled to room temperature and the solid recrystallised from ethyl acetate:hexane in the presence of activated carbon to give the desired product (2.3 g, 42%) as an orange solid.

Example 11

5-(5,6-Dichloro-3-pyridyl)-3-methyl-1,2,4-oxadiazole

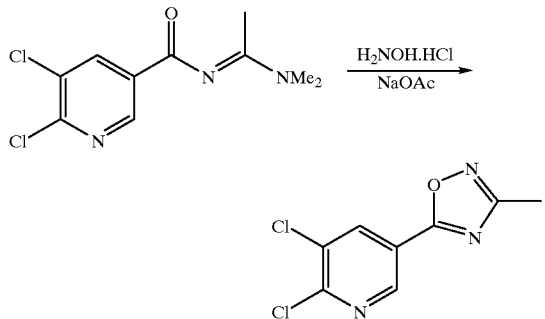

Hydroxylamine hydrochloride (0.71 g, 10 mmol) was dissolved with stirring in 5M sodium hydroxide solution (2.1 mL) and 70% acetic acid (10 mL) added. N-[1-(Dimethylamino)-ethylidene]-(5,6-dichloro-3-pyridine) carboxamide (1.95 g, 8.5 mmol) was added and the mixture stirred at room temperature over the weekend. It was then poured into water and the precipitate separated by filtration and dried to give the desired product (1.2 g, 61%) as a white solid.

Example 12

Benzeneacetamide, 2-[[[3-chloro-5-(3-methyl-1,2,4-oxadiazol-5-yl)-2-pyridinyl]oxy]methyl]-α-(methoxyimino)-N-methyl-

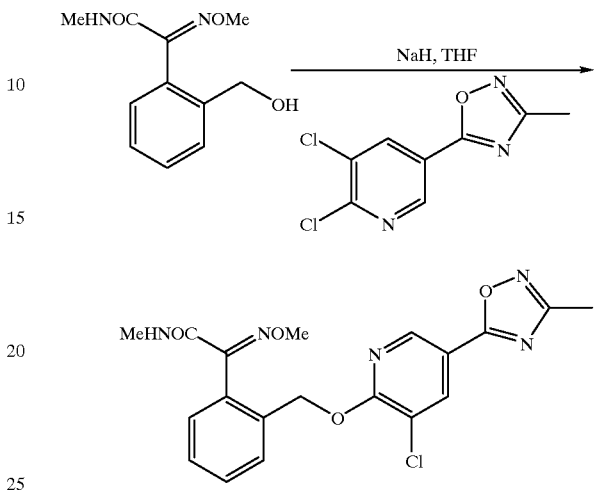

2-(Hydroxymethyl)-α-(methoxyimino)-N-methylbenzeneacetamide (0.6 g, 2.7 mmol) was dissolved with stirring in dry THF (15 mL) and 60% sodium hydride (0.12 g, 3 mmol) added. The mixture was stirred for thirty minutes and a solution of 5-(5,6-dichloro-3-pyridyl)-3-methyl-1,2,4-oxadiazole (0.62 g, 3 mmol) in dry THF (5 mL) added. The mixture was stirred at room temperature overnight and poured into water. The mixture was extracted twice with ethyl acetate (50 mL) and the organic extracts were washed twice with water (50 mL) and saturated brine (50 mL). The solution was dried over anhydrous sodium sulphate, and evaporated to dryness. Purification of the residue by chromatography over silica, eluting with 10–40% ethyl acetate:pentane, gave the desired product as a white solid (0.55 g, 49%).

Example 13

5-Methyl-6-methylthio-3-pyridinecarbonitrile

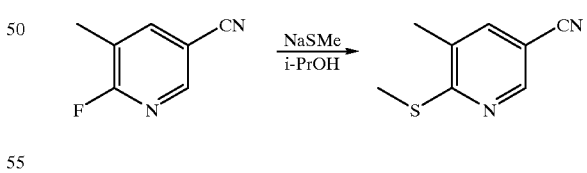

To a stirred suspension of sodium thiomethoxide (1.66 g, 23.71 mmol) in 2-propanol (20 mL) at room temperature under a nitrogen atmosphere was added a suspension of 6-fluoro-5-methyl-3-pyridinecarbonitrile (2.69 g, 19.76 mmol) in 2-propanol (10 mL). After one hour stirring at room temperature, TLC (25% EtOAc/hexane) indicated loss of starting material. The reaction mixture was diluted with water (20 mL) and filtered. The filtrate was extracted twice with ether (25 mL×2). The organic layers were combined, washed with water and evaporated in vacuo to give the desired product (2.57 g, 79.1%) as yellow fluffy crystals.

Example 14

5-Methyl-6-methylthio-3-pyridinecarboxamide

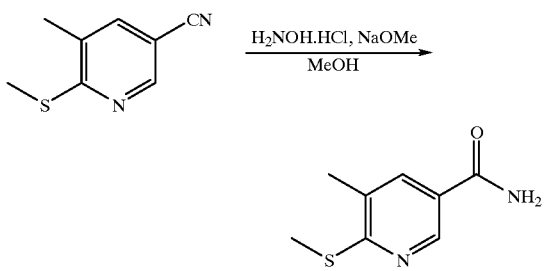

To a stirred s odiu m methoxide solution (25 wt % in methanol; 10.53 g, 48.7 mmol) diluted in dry methanol (100 mL) at room temperature under a nitrogen atmosphere was added hydroxylamine hydrochloride (3.38 g, 48.7 mmol) and 5-methyl-6-methylthio-3-pyridinecarbonitrile (2.00 g, 12.2 mmol). The white suspension was stirred at room temperature for 7 days, when it was evaporated in vacuo. The crude white solid was chromatographed on silica gel (25% EtOAc/pentane) yielding the desired product (1.66 g, 75%) as a white fluffy powder.

Example 15

Butanoic acid, 2-(5-methyl-6-methylthio-3-pyridinecarboxamido)-3-oxo, ethyl ester

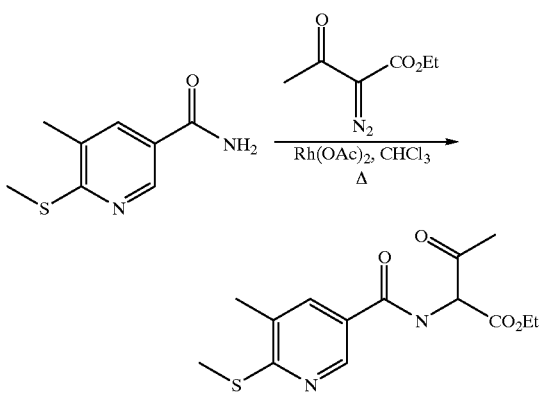

To a stirred suspension of 5-methyl-6-methylthio-3-pyridinecarboxamide (0.83 g, 4.6 mmol) in dry chloroform (120 mL) at room temperature under a nitrogen atmosphere was added rhodium (II) acetate (0.04 g, 0.09 mmol), and the reaction mixture was heated to reflux. A solution of ethyl diazoacetoacetate (1.00 g, 6.4 mmol) in dry chloroform (65 mL) was added dropwise over 6 h to the refluxing reaction mixture. After addition, the reaction mixture was kept at reflux for 30 min. The heat was removed and the reaction mixture was allowed to cool to room temperature overnight with stirring. Chromatographed on silica gel (25% EtOAc/pentane) provided the desired product (0.87 g, 90%) as a light yellow solid.

Example 16

4-Ethoxycarbonyl-5-methyl-6-(5-methyl-6-methylthio-3-pyridinyl)oxazole

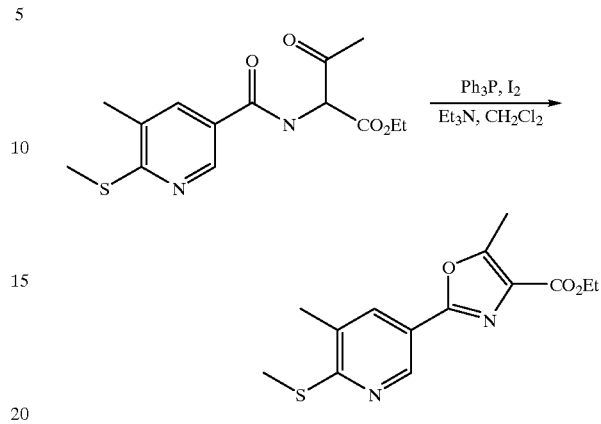

To a stirred solution of triphenylphosphine (1.30 g, 5.0 mmol) and iodine (1.26 g, 5.0 mmol) in dry dichloromethane (35 mL) at room temperature under a nitrogen atmosphere were added triethylamine (1.03 g, 10.2 mmol) and a solution of ethyl 2-(5-methyl-6-methylthio-3-pyridinecarboxamido)-3-oxo-butanoate, (0.77 g, 2.5 mmol) in dry dichloromethane (10 mL). The brown solution was stirred at room temperature for 2 hours. Chromatography on silica gel (25% EtOAc/pentane) gave the desired product (0.65 g, 89.4%) as a yellow solid.

Example 17

4-Ethoxycarbonyl-5-methyl-6-(5-methyl-6-methylsulphonyl-3-pyridinyl)oxazole

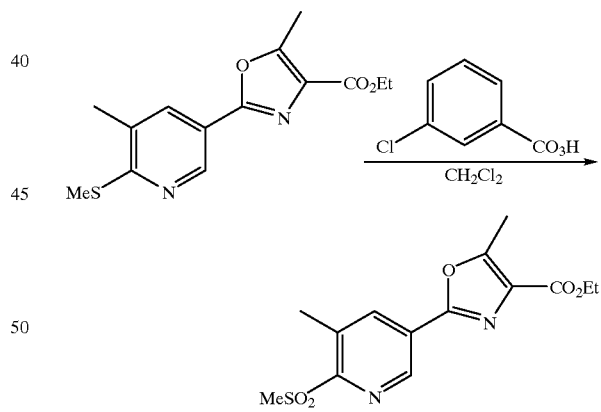

To a stirred 0° C. solution of 4-ethoxycarbonyl-5-methyl-6-(5-methyl-6-methylthio-3-pyridinyl)oxazole (0.63 g, 2.15 mmol) in dichloromethane (10 mL) under a nitrogen atmosphere was added portionwise m-chloroperbenzoic acid (1.09 g, 4.53 mmol) slurried in dichloromethane (5 mL). The ice bath was removed and the stirred white suspension was allowed to warm to room temperature. The reaction mixture was washed with aqueous sodium hydroxide (1N; 7 mL) to slightly basic. The organic layer was separated, dried over sodium sulphate, filtered and evaporated in vacuo to give the desired product (0.55 g, 78.6%) as a clear oil which solidified on standing.

Example 18

Benzeneacetamide, 2-[[[3-methyl-5-(4-ethoxycarbonyl-5-methyl-oxazol-2-yl)-2-pyridinyl]oxy]methyl]-α-(methoxyimino)-N-methyl-

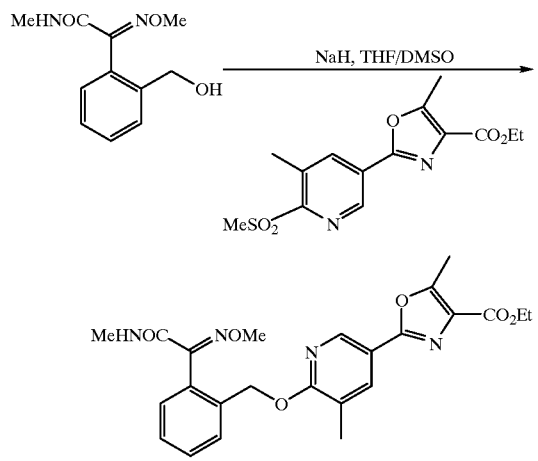

To a stirred solution of 2-(hydroxymethyl)-α-(methoxyimino)-N-methylbenzeneacetamide (0.37 g, 1.68 mmol) in dry THF (20 mL) was added sodium hydride (60% in mineral oil; 0.09 g, 2.24 mmol). The light yellow reaction mixture was stirred for 20 minutes, and a suspension of 4-ethoxycarbonyl-5-methyl-6-(5-methyl-6-methylsulphonyl-3-pyridinyl)oxazole (0.52 g, 1.85 mmol) in dry THF (5 mL)/DMSO (few drops) was added. The mixture was stirred at room temperature overnight, poured into water (25 mL) and extracted with ether (25 mL×3). The organic extracts were combined, washed with brine, dried over sodium sulphate, filtered and evaporated in vacuo. Chromatography over silica (10–35% EtOAc/pentane) gave the desired product(0.28 g, 36.1%) as a white solid.

Example 19

1-Cyclopropanecarbonyl-2-(5,6-dichloro-3-pyridinecarbonyl)-hydrazine

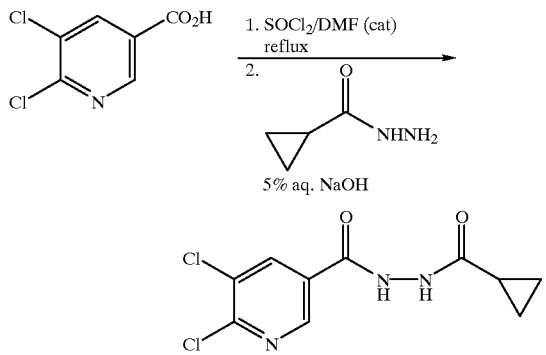

A mixture of 5,6-dichloronicotinic acid (5.2 g, 27 mmol) in thionyl chloride (50 mL) containing dimethylformamide (2 drops) was heated under reflux conditions for two hours; cooled and concentrated under reduced pressure to afford 5,6-dichloronicotinoyl chloride (5.6 g, 99%) as a yellow oil.

A mixture of cyclopropanecarboxylic acid hydrazide (1.6 g, 16 mmol) in 5% aqueous sodium hydroxide (50 mL) was cooled to 0° C. with stirring and a solution of 5,6-dichloronicotinoyl chloride (3.1 g, 14.8 mmol) in dimethoxyethane (10 mL) added over 20 minutes. This was stirred at room temperature overnight, acidified to pH 3–4 with 1N hydrochloric acid and filtered. The resulting tan solid was dried to give the desired product (1.4 g, 35%).

Example 20

2-Cyclopropyl-5-(5,6-dichloro-3-pyridinyl)-1,3,4-oxadiaxole

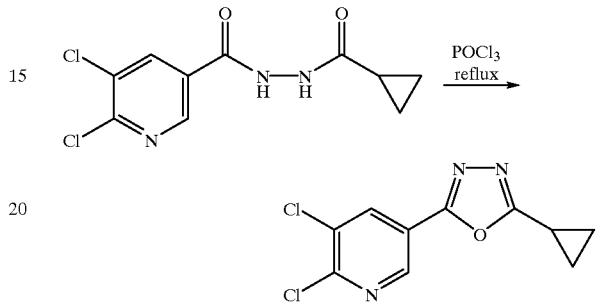

A mixture of 1-cyclopropanecarbonyl-2-(5,6-dichloro-3-pyridinecarbonyl)-hydrazine (1.2 g, 4.4 mmol) in phosphorous oxychloride (50 mL) was heated under reflux for three hours and cooled to room temperature. Excess solvent was evaporated under reduced pressure and the residue was dissolved in dichloromethane. This was washed with water and saturated sodium chloride solution, dried over anhydrous sodium sulphate, and evaporated under reduced pressure to provide the desired product (0.90 g, 80%) as a tan solid.

Example 21

Benzeneacetamide, 2-[[[3-chloro-5-(5-cyclopropyl-1,3,4-oxadiazol-2-yl)-2-pyridinyl]oxy]methyl]-α-(methoxyimino)-N-methyl-

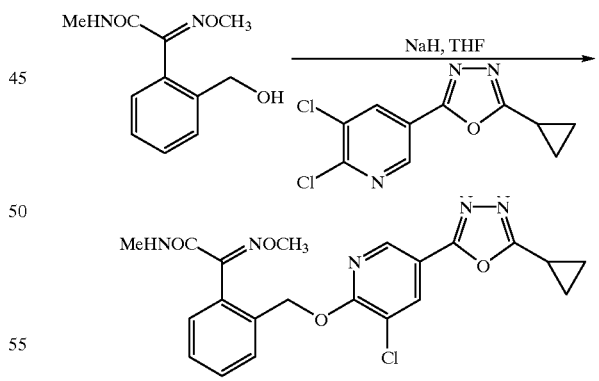

2-(Hydroxymethyl)-α-(methoxyimino)-N-methylbenzeneacetamide (0.73 g, 3.3 mmol) was dissolved with stirring in anhydrous THF (20 mL) and 60% sodium hydride (0.18 g, 4.5 mmol) added. The mixture was stirred at room temperature for one hour and a solution of 2-cyclopropyl-5-(5,6-dichloro-3-pyridinyl)-1,3,4-oxadiaxole (0.88 g, 3.3 mmol) in anhydrous THF (5 mL) added. The mixture was stirred at room temperature overnight and poured into water. The mixture was extracted twice with ethyl acetate (50 mL) and the organic extracts were washed twice with water (50 mL) and saturated brine (50 mL). The solution was dried over anhydrous sodium sulphate, and evaporated to dryness. Recrystallisation from dichloromethane:hexane gave the desired product (0.75 g, 56.6%) as off-white crystals, MP 190–191° C.

Example 22

3-Chloro-2-methylthio-5-(trimethylsilylethynyl)-pyridine

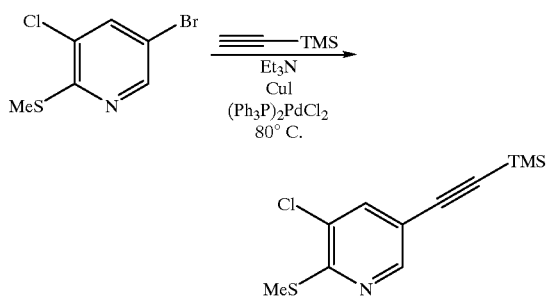

A mixture of 5-bromo-3-chloro-2-methylthio-pyridine (7.5 g, 0.031 mol), trimethylsilylacetylene (5.3 g, 0.053 mol), copper (I) iodide (60 mg, 0.32 mmol), bis(triphenylphosphine) palladium (II) chloride (0.42 g, 0.6 mmol) and triethylamine (100 mL) was sealed in a 300 mL Hastelloy steel bomb and heated with stirring at 80° C. for 17 hours. The mixture was cooled, filtered, and the precipitate washed with ethyl acetate (100 mL). The combined organic solutions were evaporated to dryness under reduced pressure. The resultant dark oil was dissolved in hexane (100 mL) and washed with water and brine, and evaporated under reduced pressure. Purification of the residue by chromatography over silica (0–2% ethyl acetate:hexane) gave the desired product (5.6 g, 71%) as a yellow oil.

Example 23

3-Chloro-5-ethynyl-2-methylthiopyridine

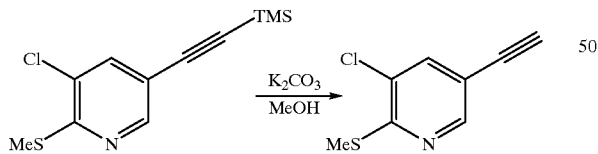

3-Chloro-2-methylthio-5-(trimethylsilylethynyl)-pyridine (1.1 g, 4.3 mmol) was dissolved with stirring in methanol (50 mL) and anhydrous potassium carbonate (2.5 g, 0.018 mol) added. The mixture was stirred overnight, filtered, and evaporated to dryness. The residue was slurried in dichloromethane (100 mL), filtered, and evaporated to dryness. The residue was purified by chromatography over silica (0–3% ethyl acetate:hexane) to give the desired product (0.78 g, 95%) as a pale solid which darkens on standing, melting point. 58–60° C.

Example 24

3-Ethyl-5-(5-chloro-6-methylthio-3-pyridyl)-isoxazole

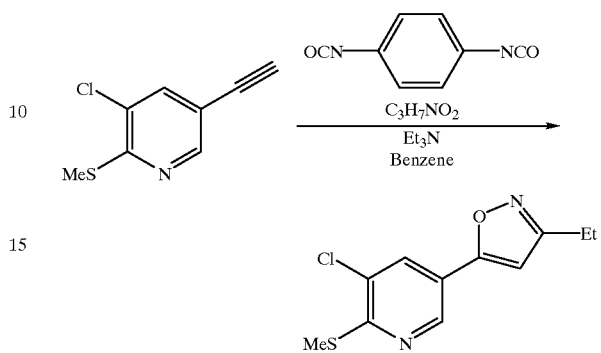

A mixture of 3-chloro-5-ethynyl-2-methylthiopyridine (0.5 g, 2.72 mmol), 1-nitropropane (0.24 g, 0.27 mmol), 1,4-phenylenediisocyanate (1.3 g, 7.93 mmol) and triethylamine (5 drops) in benzene (20 mL) was heated under reflux with stirring for 8 hours, and allowed to stir at room temperature overnight. Water (1 mL) was added and the mixture stirred at room temperature for 2 hours. It was filtered through Celite, dried over anhydrous sodium sulphate and evaporated under reduced pressure. Recrystallisation of the residue from hexane gave the desired product (0.33 g, 48%) as a cream solid, melting point. 78–80° C.

Example 25

3-Ethyl-5-(5-chloro-6-methylsulphonyl-3-pyridyl)-isoxazole

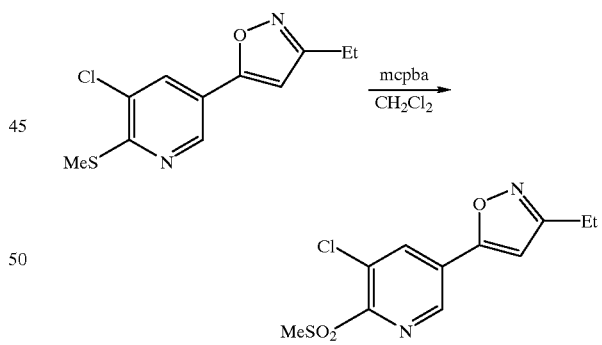

3-Ethyl-5-(5-chloro-6-methylthio-3-pyridyl)-isoxazole (0.64 g, 2.5 mmol) was dissolved with stirring in dichloromethane (50 mL) and m-chloroperoxybenzoic acid (1.59 g, 60% assay, 5.5 mmol) added. The reaction mixture was stirred overnight and 10% sodium carbonate solution (50 mL) added. The mixture was separated and the organic phase washed thrice with 2M sodium hydroxide solution (50 mL) and brine. It was dried over anhydrous sodium sulphate and evaporated under reduced pressure to give the desired product (0.67 g, 93%) as a white solid, melting point. 131–3° C.

Example 26

Benzeneacetamide, 2-[[[3-chloro-5-(3-ethyl-5-isoxazolyl)-2-pyridinyl]oxy]methyl-α-(methoxyimino)-N-methyl-

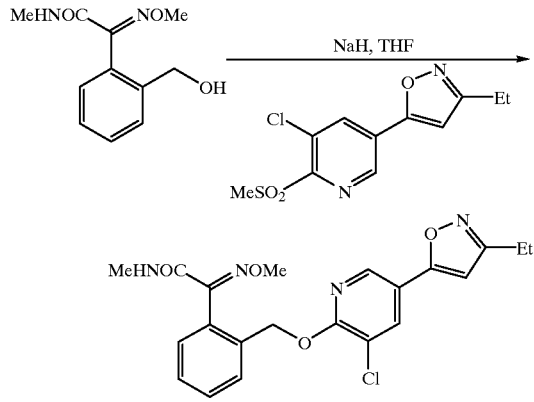

2-(Hydroxymethyl)-α-(methoxyimino)-N-methylbenzeneacetamide (0.25 g, 1.1 mmol) was dissolved with stirring in anhydrous THF (20 mL) and 60% sodium hydride (0.09 g, 2.3 mmol) added. The mixture was stirred at room temperature for 30 minutes and a solution of 5-(3-chloro-2-methylsulphonyl-5-pyridyl)-3-ethylisoxazole (0.3 g, 1.0 mmol) in anhydrous THF (15 mL) added. The resultant mixture was heated at 50° C. with stirring for 4 hours, cooled, and poured into water. It was then extracted twice with ethyl acetate (50 mL), the organic extracts combined, and washed with water (50 mL) and brine (50 mL). It was dried over anhydrous sodium sulphate, evaporated to dryness under reduced pressure, and the residue purified by chromatography over silica (5–40% ethyl acetate:hexane) to give the desired product (0.28 g, 64%) as a white solid, melting point. 124–6° C.

Example 27

5,6-Dichloro-pyridine-3-aldehyde, oxime

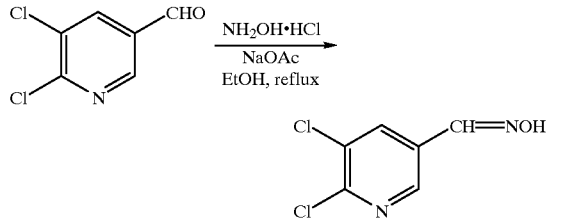

A mixture of 5,6-dichloro-pyridine-3-aldehyde (3.0 g, 0.017 mol), anhydrous sodium acetate (3.0 g, 0.037 mol), hydroxylamine hydrochloride (2.0 g, 0.029 mol) and ethanol (50 mL) was heated with stirring under reflux conditions for 3 hours. The mixture was cooled to room temperature, poured into water (250 mL) and filtered. The resulting white solid was dissolved in dichloromethane (200 mL), and the solution dried over anhydrous sodium sulphate. Evaporation of the solvent under reduced pressure and recrystallisation of the residue from ethyl acetate gave the desired product (2.90 g, 89%) as a white solid, melting point. 150–2° C.

Example 28

5,6-Dichloro-N-hydroxy-3-pyridinecarboximidoyl chloride

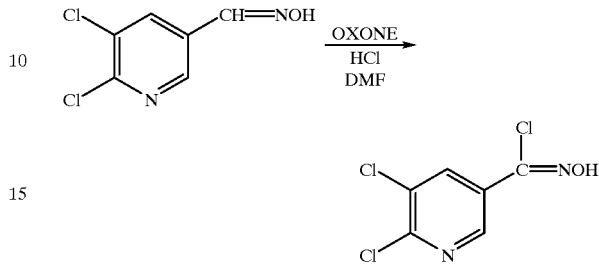

5,6-Dichloro-pyridine-3-aldehyde, oxime (0.96 g, 5 mmol) was dissolved with stirring in a 0.5M solution of hydrogen chloride in DMF (11 mL), and OXONE (1.69 g, 2.75 mmol) added. The mixture was stirred for 5 hours, additional OXONE (0.85 g, 1.38 mmol) added, and the mixture stirred overnight. It was poured into ice-water, and the resultant solid collected by filtration and dried. Recrystallisation from ethyl acetate:hexane gave the desired product (0.97 g, 86%) as a white solid, melting point. 185–6° C.

Example 29

3-(2,3-Dichloro-5-pyridyl)-5-ethylisoxazole

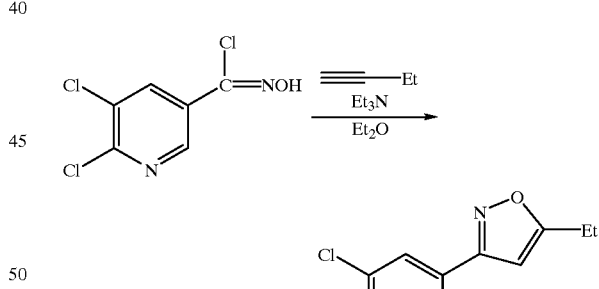

5,6-Dichloro-N-hydroxy-3-pyridinecarboximidoyl chloride (0.85 g, 3.8 mmol) was dissolved with stirring in ether (60 mL) and a solution of triethylamine (0.8 g, 7.9 mmol) in ether (50 mL) added dropwise to the solution while 1-butyne was bubbled through the reaction mixture. The mixture was stirred at room temperature overnight, filtered, and the filtrate evaporated to dryness under reduced pressure. Recrystallisation of the residue from hexane gave the desired product (0.83 g, 90%) as a cream solid, melting point. 98–9° C.

Example 30

3-(3-Chloro-2-methylthio-5-pyridyl)-5-ethylisoxazole

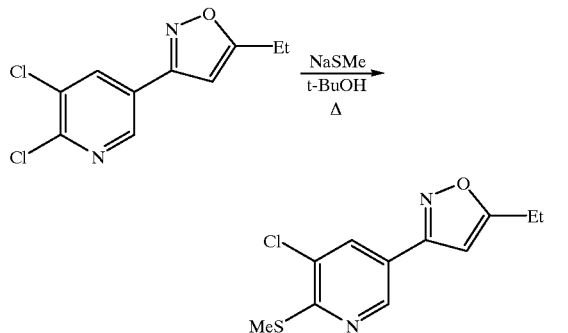

3-(2,3-Dichloro-5-pyridyl)-5-ethylisoxazole (0.71 g, 2.9 mmol) was dissolved in t-butanol (15 mL) and sodium methanethiolate (0.3 g, 4.3 mmol) added. The reaction mixture was heated under reflux with stirring for 3 hours, cooled, and poured onto ice. The resulting cream precipitate was collected by filtration, dissolved in dichloromethane (50 mL) and dried over anhydrous sodium sulphate. Evaporation of the solvent under reduced pressure gave the desired product (0.61 g, 83%) as a cream solid, melting point. 59–62° C.

Example 31

3-(3-Chloro-2-methylsulphonyl-5-pyridyl)-5-ethylisoxazole

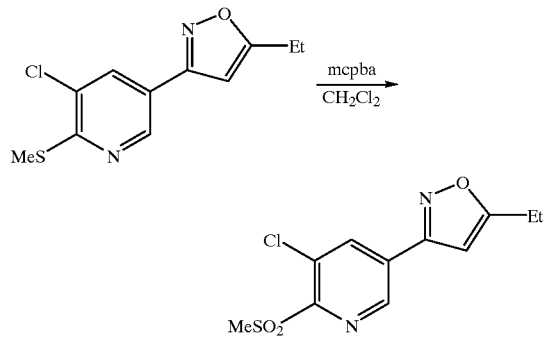

3-(3-Chloro-2-methylthio-5-pyridyl)-5-ethylisoxazole (0.55 g, 2.2 mmol) was dissolved with stirring in dichloromethane (50 mL) and m-chloroperoxybenzoic acid (1.38 g, 60% assay, 4.8 mmol) added. The mixture was stirred at room temperature for 4 hours and 10% sodium carbonate solution (50 mL) added. The mixture was separated and the organic phase washed three times with 2M sodium hydroxide solution (50 mL) and brine. It was dried over anhydrous sodium sulphate and evaporated under reduced pressure to give the desired product as a clear oil which solidifies on standing (0.57 g, 90%).

Example 32

Benzeneacetamide, 2-[[[3-chloro-5-(5-ethyl-3-isoxazolyl)-2-pyridinyl]oxy]methyl-α-(methoxyimino)-N-methyl-

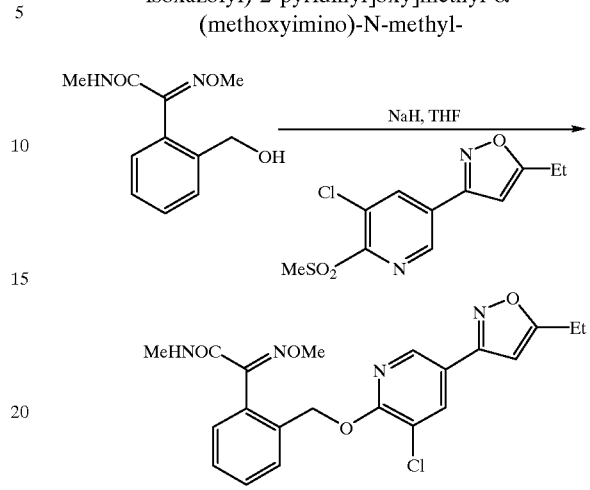

2-(Hydroxymethyl)-α-(methoxyimino)-N-methylbenzeneacetamide (0.43 g, 1.9 mmol) was dissolved with stirring in anhydrous THF (20 mL) and 60% sodium hydride (0.15 g, 3.75 mmol) added. The mixture was stirred at room temperature for 30 minutes and a solution of 3-(3-chloro-2-methylsulphonyl-5-pyridyl)-5-ethylisoxazole (0.5 g, 1.74 mmol) in anhydrous THF (15 mL) added. He resultant mixture was heated at 50° C. with stirring for 4 for hours, cooled, and poured into water. It was then extracted twice with ethyl acetate (50 mL), the organic extracts combined, and washed with water (50 mL) and brine (50 mL). It was dried over anhydrous sodium sulphate, evaporated to dryness under reduced pressure, and the residue purified by chromatography over silica (5–40% ethyl acetate:hexane) to give the desired product (0.55 g, 68%) as a white solid, melting point. 143–5° C.

The following tables identifies several compounds of formula (1) prepared analogous to the various procedures illustrated in the preceding examples:

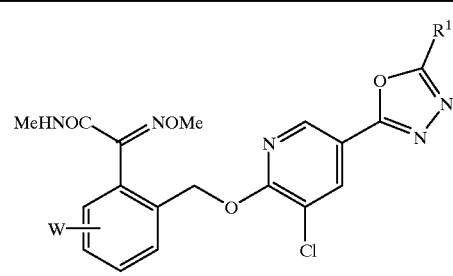

| Example | W | R1 |
|---|---|---|
| 1 | H | cyclopropyl |
| 2 | H | phenyl |
| 3 | H | methyl |
| 4 | H | t-butyl |
| 5 | H | ethyl |

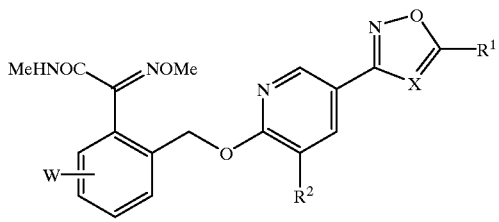

| Example | W | X | R² | R³ |
|---|---|---|---|---|
| 6 | H | N | t-butyl | Cl |
| 7 | H | N | phenyl | Cl |
| 8 | H | N | methyl | Cl |
| 9 | H | N | t-butyl | H |
| 10 | H | N | methyl | H |
| 11 | H | N | trifluoromethyl | Cl |
| 12 | H | N | phenyl | H |
| 13 | H | N | cyclopentyl | Cl |
| 14 | H | N | 3-heptyl | Cl |
| 15 | H | N | 1-adamantyl | Cl |
| 16 | H | N | trifluoromethyl | H |
| 17 | H | N | neopentyl | Cl |
| 18 | H | N | 2-furyl | Cl |
| 19 | H | N | 1-chloro-2,2-dimethylethyl | Cl |
| 20 | H | N | 2-thienyl | Cl |
| 21 | H | N | cyclopropyl | Cl |
| 22 | H | N | 1-butenyl | Cl |
| 23 | H | N | methoxymethyl | Cl |
| 24 | H | N | phenylthiomethyl | Cl |
| 25 | H | N | methoxymethyl | H |
| 26 | H | N | 2-chloroethyl | Cl |
| 27 | 3-F | N | t-butyl | Cl |
| 28 | H | N | phenylthiomethyl | H |
| 29 | 3-Cl | N | t-butyl | Cl |
| 30 | 3-F | N | methyl | Cl |
| 31 | 4-OMe | N | trifluoromethyl | Cl |
| 32 | 3-F | N | trifluoromethyl | Cl |
| 33 | 4-CH₃ | N | trifluoromethyl | Cl |
| 34 | 3-Cl | N | trifluoromethyl | Cl |
| 35 | 3-CH₃ | N | trifluoromethyl | Cl |
| 36 | H | N | ethyl | Cl |
| 37 | H | N | isopropyl | Cl |
| 38 | H | CH | isopropyl | Cl |
| 39 | H | CH | ethyl | Cl |
| 40 | H | CH | ethoxy | Cl |
| 41 | H | CH | t-butyl | Cl |
| 42 | H | CH | isopropyl | H |
| 43 | H | CH | t-butyl | H |
| 44 | H | CH | phenyl | H |
| 45 | H | CH | methyl | H |
| 46 | H | CH | ethyl | H |

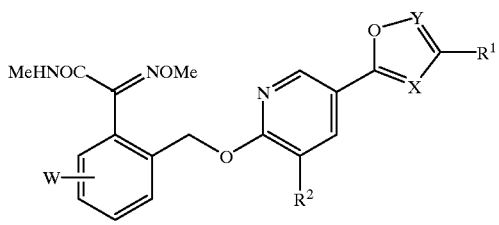

| Example | W | X | Y | R¹ | R² |
|---|---|---|---|---|---|
| 47 | H | N | N | t-butyl | Cl |
| 48 | H | N | N | phenyl | Cl |
| 49 | H | N | N | methyl | Cl |
| 50 | 3-F | N | N | methyl | Cl |

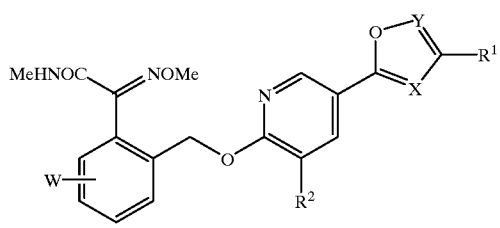

-continued

| Example | W | X | Y | R¹ | R² |
|---|---|---|---|---|---|
| 51 | 3-Cl | N | N | methyl | Cl |
| 52 | H | N | C—CH₃ | ethoxycarbonyl | CH₃ |
| 53 | H | N | N | cyclopropyl | Cl |
| 54 | H | N | N | ethyl | Cl |
| 55 | 3-Cl | N | N | t-butyl | Cl |
| 56 | 3-F | N | N | t-butyl | Cl |
| 57 | H | N | N | Phenoxymethyl | Cl |
| 58 | H | N | N | Phenylthiomethyl | Cl |
| 59 | H | N | N | isopropyl | Cl |
| | H | N | N | t-butyl | CH₃ |
| 61 | H | N | N | Methoxymethyl | Cl |
| 62 | H | N | N | Methylthiomethyl | Cl |
| 63 | H | N | N | ethyl | H |
| 64 | H | N | N | Dimethylamino | Cl |
| 65 | H | N | N | t-butyl | H |
| 66 | 3-Cl | N | N | ethyl | Cl |
| 67 | 3-F | N | N | ethyl | Cl |
| 68 | H | N | N | Trifluoromethyl | Cl |
| 69 | H | N | N | Piperidinyl | Cl |
| 70 | H | N | N | isopropyl | H |
| 71 | H | N | N | Trifluoromethyl | H |
| 72 | H | N | N | cyclohexyl | Cl |
| 73 | H | N | N | cyclohexyl | H |
| 74 | H | N | N | n-propyl | H |
| 75 | H | N | N | i-butyl | H |
| 76 | H | CH | N | ethyl | Cl |
| 77 | H | N | N | i-butyl | Cl |
| 78 | H | N | N | n-propyl | Cl |
| 79 | H | CH | N | methyl | Cl |
| 80 | H | CH | N | ethyl | H |

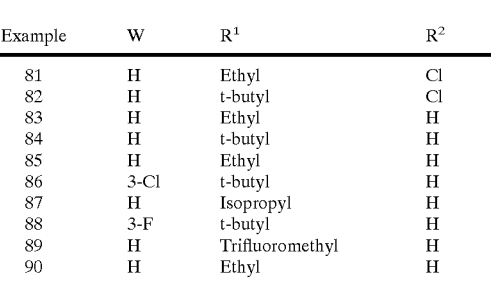

| Example | W | R¹ | R² |
|---|---|---|---|
| 81 | H | Ethyl | Cl |
| 82 | H | t-butyl | Cl |
| 83 | H | Ethyl | H |
| 84 | H | t-butyl | H |
| 85 | H | Ethyl | H |
| 86 | 3-Cl | t-butyl | H |
| 87 | H | Isopropyl | H |
| 88 | 3-F | t-butyl | H |
| 89 | H | Trifluoromethyl | H |
| 90 | H | Ethyl | H |

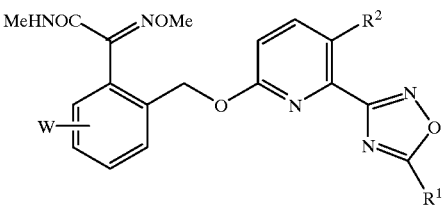

| Example | W | R¹ | R² |
|---|---|---|---|
| 91 | H | t-butyl | H |
| 92 | H | Methyl | H |
| 93 | H | Trifluoromethyl | H |
| 94 | H | Methoxymethyl | H |
| 95 | H | Ethoxycarbonyl | H |
| 96 | H | Phenyl | H |

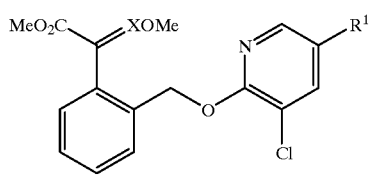

| Example | X | R¹ |
|---|---|---|
| 97 | N | 5-t-butyl-1,2,4-oxadiazol-3-yl |
| 98 | CH | 5-t-butyl-1,2,4-oxadiazol-3-yl |
| 99 | CH | 3-ethyl-1,2,4-oxadiazol-5-yl |
| 100 | CH | 3-t-butyl-1,2,4-oxadiazol-5-yl |
| 101 | N | 3-ethyl-1,2,4-oxadiazol-5-yl |

The compounds of formula (1) thus produced are usually obtained as a mixture of the E and Z forms, which can then be separated, via standard means known in the art, into each of those forms, if desired.

The compounds of formula (1) show strong fungicidal activity against a wide variety of fungi. The following tests illustrate the fungicidal efficacy of the compounds of this invention.

Fungicide Utility

The compounds of the present invention have been found to control fungi, particularly plant pathogens. When employed in the treatment of plant fungal diseases, the compounds are applied to the plants in a disease inhibiting and phytologically acceptable amount. Application may be performed before and/or after the infection with fungi on plants. Application may also be made through treatment of seeds of plants, soil where plants grow, paddy fields for seedlings, or water for perfusion. The compounds may also be employed effectively for the control of fungi on wood, leather, carpet backings, or in paint.

As used herein, the term "disease inhibiting and phytologically acceptable amount", refers to an amount of a compound of the present invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds per acre.

The compounds of the invention may also be used to protect stored grain and other non-plant loci from fungal infestation.

The following experiments were performed in the laboratory to determine the fungicidal efficacy of the compounds of the invention.

Compound Formulation: Compound formulation was accomplished by dissolving technical materials in acetone, with serial dilutions then made in acetone to obtain desired rates. Final treatment volumes were obtained by adding nine volumes 0.05% aqueous Tween-20 or Triton X-100, depending upon the pathogen.

Late Blight of Tomatoes (*Phytophthora infestans*—PHYTIN): Tomatoes (cultivar Rutgers) were grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Phytophthora infestans*. The plants were then transferred to the greenhouse until disease developed on the untreated control plants.

Powdery Mildew of Wheat (*Erysiphe graminis*—ERYSGT): Wheat (cultivar Monon) was grown in a soilless peat-based potting mixture (Metromix) until the seedlings were 1–2 leaf (BBCH 12). These plants were then sprayed to run off with the test compound at a rate of 100 ppm. After 24 hours the test plants were inoculated with *Erysiphe graminis* by dusting spores from stock plants onto the test plants. The plants were then transferred to the greenhouse until disease developed on the untreated control plants.

Glume blotch of wheat (*Leptosphaeria nodorum*—LEPTNO): Wheat (cultivar Monon) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Leptosphaeria nodorum*. The plants were then transferred to the greenhouse until disease developed on the untreated control plants.

Brown rust (*Puccinia recondita*—PUCCRT): Wheat (cultivar Monon) was grown from seed in a soilless peat-based potting mixture (Metromix) until the seedlings were 1–2). These plants were then sprayed to run off with the test compound at a rate of 100 ppm. After 24 hours the test plants were inoculated with an aqueous spore suspension of *Puccinia recondita*. The plants were then transferred to the greenhouse until disease developed on the untreated control plants.

the following table presents the activity of typical compounds of the present invention when evaluated in these experiments. The effectiveness of the test compounds in controlling disease was rated using the following scale:

| Example | ERYSGT 1DP | LEPTNO 1DP | PHYTIN 1DP | PUCCRT 1DP |
|---------|------------|------------|------------|------------|
| 1 | - | - | ++ | ++ |
| 2 | + | ++ | ++ | ++ |
| 3 | ++ | ++ | ++ | ++ |
| 4 | ++ | ++ | - | ++ |
| 5 | ++ | ++ | ++ | ++ |
| 6 | ++ | ++ | ++ | ++ |
| 7 | ++ | ++ | ++ | ++ |
| 8 | ++ | ++ | - | ++ |
| 9 | ++ | ++ | - | ++ |
| 10 | ++ | ++ | - | ++ |
| 11 | ++ | ++ | - | ++ |
| 12 | ++ | ++ | ++ | ++ |
| 13 | ++ | ++ | - | ++ |
| 14 | ++ | ++ | - | ++ |
| 15 | ++ | - | ++ | ++ |
| 16 | ++ | - | - | ++ |
| 17 | ++ | ++ | - | ++ |
| 18 | + | ++ | ++ | ++ |
| 19 | ++ | ++ | - | ++ |
| 20 | ++ | - | ++ | ++ |
| 21 | ++ | ++ | ++ | ++ |
| 22 | ++ | ++ | - | ++ |
| 23 | ++ | + | - | ++ |
| 24 | - | ++ | ++ | ++ |
| 25 | ++ | + | ++ | ++ |
| 26 | ++ | ++ | ++ | ++ |
| 27 | ++ | ++ | - | ++ |
| 28 | ++ | ++ | ++ | ++ |
| 29 | ++ | ++ | - | ++ |
| 30 | ++ | ++ | - | ++ |
| 31 | ++ | ++ | - | ++ |
| 32 | ++ | + | - | ++ |
| 33 | ++ | ++ | ++ | ++ |
| 34 | ++ | ++ | - | ++ |
| 35 | ++ | ++ | - | ++ |
| 36 | ++ | ++ | - | ++ |
| 37 | ++ | ++ | - | ++ |
| 38 | ++ | ++ | - | ++ |
| 39 | ++ | ++ | - | ++ |
| 40 | ++ | - | + | ++ |
| 41 | ++ | ++ | - | ++ |
| 42 | ++ | - | ++ | ++ |
| 43 | ++ | ++ | ++ | ++ |
| 44 |  |  | - |  |
| 45 |  |  | + |  |
| 47 | ++ | ++ | - | ++ |
| 48 | ++ | + | ++ | ++ |
| 49 | ++ | ++ | - | ++ |
| 50 | ++ | + | - | ++ |
| 51 | ++ | - | - | ++ |
| 52 | + | + | ++ | ++ |
| 53 | ++ | + | ++ | ++ |
| 54 | ++ | ++ | ++ | ++ |
| 55 | ++ | ++ | - | ++ |
| 56 | ++ | ++ | - | ++ |
| 57 | ++ | + |  | ++ |
| 58 | ++ | ++ |  | ++ |
| 59 | ++ | ++ |  | ++ |
| 60 | ++ | ++ |  | ++ |
| 61 | ++ | - |  | ++ |
| 62 | ++ | ++ |  | ++ |
| 63 | ++ | + |  | ++ |
| 64 | ++ | ++ | - | ++ |
| 65 | ++ | ++ | - | ++ |
| 66 | ++ | ++ | - | ++ |
| 67 | + | ++ | - | ++ |
| 68 | ++ | ++ | - | ++ |
| 69 | ++ | ++ | ++ | ++ |
| 70 | ++ | ++ | - | ++ |
| 71 | ++ | - | ++ | ++ |
| 72 | - | - | - | ++ |
| 73 | ++ | - | + | ++ |
| 74 | ++ | - | - | ++ |
| 75 | ++ | + | - | ++ |
| 76 | ++ | ++ | + | ++ |
| 77 | ++ | ++ | - | ++ |
| 78 | ++ | ++ | - | ++ |
| 79 |  |  | - |  |
| 80 |  |  | - |  |
| 81 | ++ | + | + | ++ |
| 82 | ++ | ++ | ++ | ++ |
| 83 | + | ++ | ++ | ++ |
| 84 | + | ++ | ++ | ++ |
| 85 | + | - | - | ++ |
| 86 | ++ | - | + | ++ |
| 87 | ++ | ++ | ++ | ++ |
| 88 | ++ | ++ | ++ | ++ |
| 89 | - | - | ++ | ++ |
| 97 | ++ | ++ | ++ | ++ |
| 98 | ++ | ++ | - | ++ |
| 99 | ++ | ++ | + | ++ |
| 100 | + | + | ++ | ++ |
| 101 | ++ | + | ++ | ++ | blank space = not tested
− = 0–24% control of plant disease
+ = 25–74% control of plant disease
++ = 75–100% control of plant disease The compounds of this invention are preferably applied in the form of a composition comprising one or more of the compounds of formula (1) with a phytologically-acceptable carrier. The compositions are either concentrated formulations which are dispersed in water or another liquid for application, or are dust or granular formulations which are applied without further treatment. The compositions are prepared according to procedures which are conventional in the agricultural chemical art, but which are novel and important because of the presence therein of the compounds of this invention. Some description of the formulation of the compositions is given to assure that agricultural chemists can readily prepare desired compositions.

The dispersions in which the compounds are applied are most often aqueous suspensions or emulsions prepared from concentrated formulations of the compounds. Such water-soluble, water suspendable, or emulsifiable formulations are either solids, usually known as wettable powders, or liquids, usually known as emulsifiable concentrates or aqueous suspensions. The present invention contemplates all vehicles by which the compounds of this invention can be formulated for delivery for use as a fungicide. As will be readily appreciated, any material to which these compounds can be added may be used, provided they yield the desired utility without significant interference with activity of the compounds of this invention as antifungal agents.

Wettable powders, which may be compacted to form water dispersible granules, comprise an intimate mixture of the active compound, an inert carrier and surfactants. The concentration of the active compound is usually from about 10% to about 90% w/w, more preferably about 25% to about 75% w/w. In the preparation of wettable powder compositions, the toxicant products can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the toxicant in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the compounds of this invention comprise a convenient concentration, such as from about 10% to about 50% w/w, in a suitable liquid. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilised with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface active dispersing agents are usually employed in liquid compositions and in the amount of from 0.1 to 20 percent by weight of the combined weight of the dispersing agent and active compound. The active compositions can also contain other compatible additives, for example, plant growth regulators and other biologically active compounds used in agriculture.

Aqueous suspensions comprise suspensions of water-insoluble compounds of this invention, dispersed in an aqueous vehicle at a concentration in the range from about 5% to about 50% w/w. Suspensions are prepared by finely grinding the compound, and vigorously mixing it into a vehicle comprised of water and surfactants chosen from the same types above discussed. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The compounds may also be applied as granular compositions, which are particularly useful for applications to the soil. Granular compositions usually contain from about 0.5% to about 10% w/w of the compound, dispersed in an inert carrier which consists entirely or in large part of coarsely divided attapulgite, bentonite, diatomite, clay or a similar inexpensive substance. Such compositions are usually prepared by dissolving the compound in a suitable solvent and applying it to a granular carrier which has been preformed to the appropriate particle size, in the range of from about 0.5 to about 3 mm. Such compositions may also be formulated by making a dough or paste of the carrier and compound, and crushing and drying to obtain the desired granular particle.

Dusts containing the compounds are prepared simply by intimately mixing the compound in powdered form with a suitable dusty agricultural carrier, such as, for example, kaolin clay, ground volcanic rock, and the like. Dusts can suitably contain from about 1% to about 10% w/w of the compound.

The active compositions may contain adjuvant surfactants to enhance deposition, wetting and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The composition may optionally include fungicidal combinations which comprise at least 1% of one or more of the compounds of this invention with another pesticidal compound. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments the other pesticidal compound is employed as a supplemental toxicant for the same or for a different pesticidal use. The compounds in combination can generally be present in a ratio of from 1:100 to 100:1.

The present invention includes within its scope methods for the control or prevention of fungal attack. These methods comprise applying to the locus of the fungus, or to a locus in which the infestation is to be prevented (for example applying to cereal or grape plants), a fungicidal amount of one or more of the compounds of this invention or compositions. The compounds are suitable for treatment of various plants at fungicidal levels, while exhibiting low phytotoxicity. The compounds are useful in a protectant or eradicant fashion. The compounds of this invention are applied by any of a variety of known techniques, either as the compounds or as compositions including the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds of this invention have been found to have significant fungicidal effect particularly for agricultural use. Many of the compounds are particularly effective for use with agricultural crops and horticultural plants, or with wood, paint, leather or carpet backing.

In particular, the compounds effectively control a variety of undesirable fungi which infect useful plant crops. Activity has been demonstrated for a variety of fungi, including for example the following representative fungi species: Downy Mildew of Grape (*Plasmopara viticola*—PLASVI), Late Blight of Tomato (*Phytophthora infestans*—PHYTIN), Apple Scab (*Venturia inaequalis*—VENTIN), Brown Rust of Wheat (*Puccinia Recondita*—PUCCRT), Stripe Rust of Wheat (*Puccinia striiformis*—PUCCST), Rice Blast (*Pyricularia oryzae*—PYRIOR), Cercospora Leaf Spot of Beet (*Cercospora beticola*—CERCBE), Powdery Mildew of Wheat (*Erysiphe graminis*—ERYSGT), Leaf Blotch of Wheat (*Septoria tritici*—SEPTTR), Sheath Blight of Rice (*Rhizoctonia solani*—RHIZSO), Eyespot of Wheat (*Pseudocercosporella herpotrichoides*—PSDCHE), Brown Rot of Peach (*Monilinia fructicola*—MONIFC), Glume Blotch of Wheat (*Septoria nodorum*—LEPTNO). It will be understood by those in the art that the efficacy of the compounds of this invention for the foregoing fungi establishes the general utility of the compounds as fungicides.

The compounds of this invention have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the toxic active ingredient. Thus, all the active ingredients of the compounds of this invention, and compositions containing the same, may not be equally effective at similar concentrations or against the same fungal species. The compounds of this invention and compositions are effective in use with plants in a disease inhibiting and phytologically acceptable amount. The term "disease inhibiting and phytologically acceptable amount" refers to an amount of a compound which kills or inhibits the plant disease for which control is desired, but is not significantly toxic to the plant. This amount will generally be from about 1 to about 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre.

What is claimed is:

1. A compound of Formula (1)

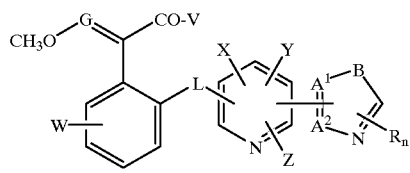

Formula (1)

wherein

L is —$CH_2$—, —$CH_2O$—, —$OCH_2$—, —$CH_2S$—, —$SCH_2$—, —CH=CH—, —C≡C—, or

, wherein n is an integer 0–2;

X, Y, and Z are each independently H, $C_{1-6}$ alkyl, $C_{1-6}$ alkoxy, halo-$C_{1-6}$ alkyl, halo-$C_{1-6}$ alkoxy, halo, nitro, carbo-$C_{1-6}$ alkoxy, cyano, $C_{1-6}$ alkylthio, or halo-$C_{1-6}$ alkylthio;

W is H, halogen, $C_{1-4}$ alkyl, $C_{1-4}$ alkoxy, halo-$C_{1-4}$ alkyl, or $C_{1-4}$ alkylthio;

R is H, $C_{1-10}$ alkyl, alkenyl cycloalkyl, haloalkyl, alkoxyalkyl, optionally substituted phenoxyalkyl, alkylthioalkyl, optionally substituted phenylthioalkyl, cyanoalkyl, optionally substituted benzyl, alkoxycarbonyl, optionally substituted phenyl, optionally substituted heterocycle, n is 0–2;

$A^1$, $A^2$ are independently N, $CR^1$;

B is O, S, $NR^1$;

G is CH or N;

V is $OCH_3$ or $NHCH_3$;

$R^1$ is $C_{1-6}$ alkyl, $C_{1-6}$ alkenyl, $C_{1-6}$ alkynyl, optionally substituted phenyl, optionally substituted benzyl.

2. A compound of claim 1 of the formula

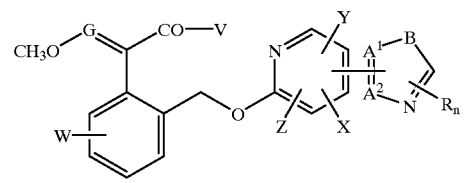

wherein the substituents are as defined in claim 1.

3. A compound of claim 2 of the formula

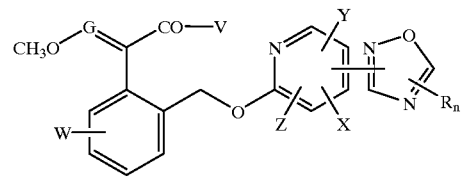

wherein the substituents are as defined in claim 1.

4. A compound of claim 3 of the formula

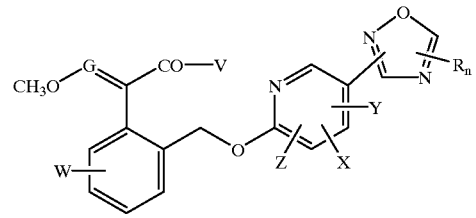

wherein the substituents are as defined in claim 1.

5. A compound of claim 4 of the formula

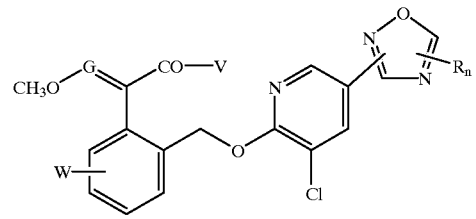

wherein the substituents are as defined in claim 1.

6. A compound of claim 5 of the formula

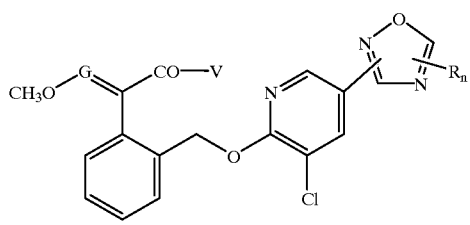

wherein the substituents are as defined in claim 1.

7. A compound of claim 6 of the formula

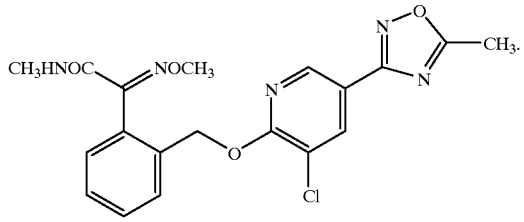

8. A compound of claim 6 of the formula

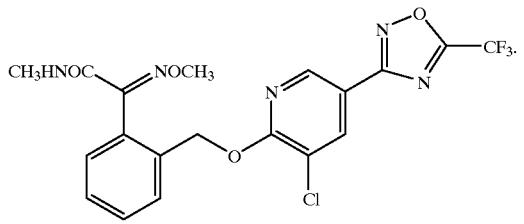

9. A compound of claim 6 the formula

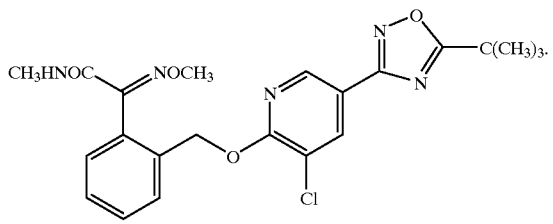

10. A compound of claim 6 of the formula

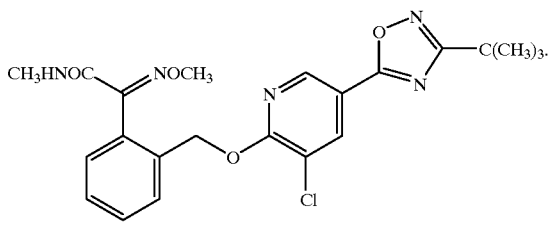

11. A compound of claim 6 the formula

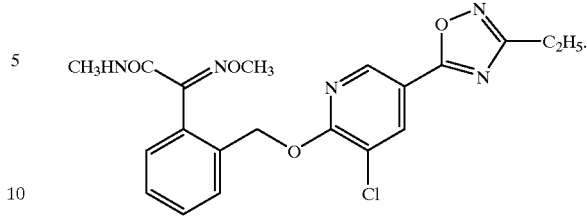

12. A compound of claim 6 of the formula

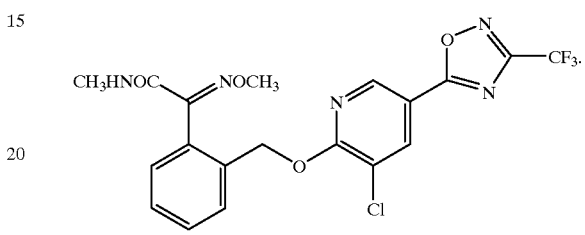

13. A compound of claim 6 of the formula

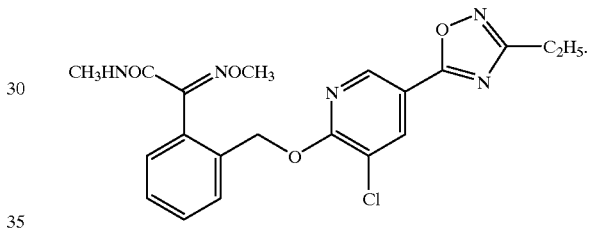

14. A fungicidal method which comprises applying to the locus to be treated a fungicidally-effective amount of a compound of formula (1)

Formula (1)

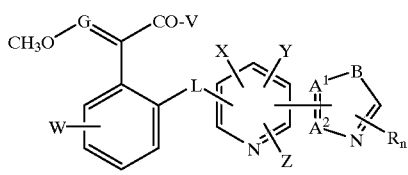

wherein
L is —CH$_2$—, —CH$_2$O—, —OCH$_2$—, —CH$_2$S—, —SCH$_2$—, —CH=CH—, —C≡C—, or

, wherein
n is an integer 0–2;
X, Y, and Z are each independently H, C$_{1-6}$ alkyl, C$_{1-6}$ alkoxy, halo-C$_{1-6}$ alkyl, halo-C$_{1-6}$ alkoxy, halo, nitro, carbo-C$_{1-6}$ alkoxy, cyano, C$_{1-6}$ alkylthio, or halo-C$_{1-6}$ alkylthio;
W is H, halogen, C$_{1-4}$ alkyl, C$_{1-4}$ alkoxy, halo-C$_{1-4}$ alkyl, or C$_{1-4}$ alkylthio;

R is H, $C_{1-10}$ alkyl, alkenyl cycloalkyl, haloalkyl, alkoxyalkyl, optionally substituted phenoxyalkyl, alkylthioalkyl, optionally substituted phenlythioalkyl, cyanoalkyl, optionally substituted benzyl, alkoxycarbonyl, optionally substituted phenyl, optionally substituted heterocycle n is 0–2;

$A^1$, $A^2$ are independently N, $CR^1$;

B is O, S, $NR^1$;

G is CH or N;

V is $OCH_3$ or $NHCH_3$;

$R^1$ is $C_{1-6}$ alkyl, $C_{1-6}$ alkenyl, $C_{1-6}$ alkynyl, optionally substituted phenyl, optionally substituted benzyl.

* * * * *